(12) United States Patent
Hill

(10) Patent No.: US 7,304,731 B2
(45) Date of Patent: Dec. 4, 2007

(54) SYSTEMS AND METHODS FOR PROVIDING ILLUMINATION OF A SPECIMEN FOR INSPECTION

(75) Inventor: Andrew V. Hill, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 274 days.

(21) Appl. No.: 11/219,014

(22) Filed: Sep. 2, 2005

(65) Prior Publication Data
US 2007/0052953 A1 Mar. 8, 2007

(51) Int. Cl.
*G01N 21/88* (2006.01)
(52) U.S. Cl. .................................. 356/237.2; 362/259
(58) Field of Classification Search ............ 356/237.1, 356/237.2, 237.3, 237.4, 237.5; 362/259, 362/553; 359/559
See application file for complete search history.

(56) References Cited

U.S. PATENT DOCUMENTS 6,672,739 B1 * 1/2004 Argyle et al. ............... 362/259

7,001,055 B1 * 2/2006 Lange ....................... 362/551

OTHER PUBLICATIONS

U.S. Appl. No. 11/228,584 entitled Fourier Filters and Wafer Inspection Systems.

* cited by examiner

*Primary Examiner*—Richard A. Rosenberger
(74) *Attorney, Agent, or Firm*—Baker & McKenzie LLP

(57) ABSTRACT

Systems and methods for providing illumination of a specimen for inspection are provided. One system includes one or more first optical elements configured to illuminate a diffuser with a predetermined pattern of coherent light. The system also includes one or more second optical elements configured to image light exiting the diffuser onto an illumination pupil of the system such that the predetermined pattern is reproduced in the illumination pupil. In addition, the system includes an objective lens configured to focus light from the predetermined pattern in the illumination pupil onto a specimen plane. In one embodiment, the light focused onto the specimen plane is not substantially coherent. In another embodiment, the predetermined pattern is selected based on an illumination mode selected for the inspection of the specimen.

28 Claims, 5 Drawing Sheets

SYSTEMS AND METHODS FOR PROVIDING ILLUMINATION OF A SPECIMEN FOR INSPECTION

BACKGROUND OF THE INVENTION

1. Field of the Invention

This invention generally relates to systems and methods for providing illumination of a specimen for inspection. Certain embodiments relate to a system configured to illuminate a diffuser with a predetermined pattern of coherent laser light and to image light exiting the diffuser onto an illumination pupil of the system thereby reproducing the predetermined pattern at the illumination pupil.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

One obvious way to improve the detection of relatively small defects is to increase the resolution of an optical inspection system. One way to increase the resolution of an optical inspection system is to decrease the wavelength at which the system can operate. As the wavelength of inspection systems decrease, incoherent light sources are incapable of producing light with sufficient brightness. Using light sources that have sufficient brightness is important to successful inspection since using a light source with relatively low brightness can reduce the sensitivity of the inspection system. In particular, when using a relatively low brightness light source, the signal-to-noise ratio of output signals generated by the inspection system may be too low for accurate defect detection. To mitigate the effects of a low brightness light source on the output signals of an inspection system, the throughput of inspection may be reduced to allow enough light to be collected. Obviously, reduced throughput for inspection is highly undesirable.

Accordingly, for inspection systems that are designed to operate at smaller wavelengths, a more suitable light source is a laser light source that can generate relatively bright light at relatively small wavelengths. However, laser light sources generate coherent light. Such light is disadvantageous for inspection since coherent light can produce speckle in images of a specimen generated by the system. Since speckle is a source of noise in the images, the signal-to-noise ratio of output signals generated by the inspection system will be reduced by speckle. Therefore, many illumination systems have been developed for inspection applications that reduce the speckle of light from laser light sources.

Coherent light is also disadvantageous in imaging-based inspection systems since the coherent light can produce ringing in images generated by the inspection systems. In particular, coherent light will produce sharp transitions in the images instead of smooth transitions. These sharp transitions can produce artifacts in inspection images that will increase the difficulty of detecting defects in the inspection images. Reducing the coherence of the light such that the specimen is illuminated with incoherent or partially coherent light will decrease the aberrations in the images of the specimen. Therefore, for inspection applications, many illumination systems have been developed that reduce the coherence of the light generated by a coherent light source before the light impinges on the specimen.

One illumination system that can be used with a coherent light source includes a diffuser that is illuminated by a coherent laser beam. In one such illumination system, the surface of the diffuser is imaged onto the entrance of a homogenizing rod. The Fourier transform plane of the diffuser surface is imaged into the system pupil, and the exit of the homogenizing rod is imaged into the system field. In such a system, the scatter distribution from the diffuser determines the light distribution in the system pupil. Speckle modulation in the image is minimized by rotating the diffuser during the integration time of the imaging sensor.

Another illumination system that can be used with a coherent light source includes a coherent laser beam that is scanned around the system pupil using galvo mirrors, a spinning polygon mirror, or a holographic scanner. The divergence angle of the spot in the pupil establishes the distribution of light in the field. The resulting image is a sum of all of the coherent images formed during the integration time of the imaging sensor.

Yet another illumination system that can be used with a coherent light source includes a stationary or rotating diffuser that is illuminated by a coherent laser beam. The diffused beam is scanned around the system pupil by galvo mirrors positioned at the Fourier transform plane of the diffuser. The diffuser surface is imaged into the entrance of a homogenizing rod. The resulting image is a sum of all of the coherent images formed during the integration time of the imaging system.

Each of the illumination systems described above, however, has at least one of the following disadvantages. For example, the distribution of light in the pupil is difficult to control. Specific distributions of light can be generated in the pupil using apertures, but light is lost due to the blocking of the light by the apertures. In another example, the distribution of light in the field is not uniform. Better uniformity can be achieved by sacrificing light and illuminating an area that is larger than the field of view of the imaging sensor. In an additional example, power densities are high on surfaces near pupil planes. High power densities can hasten surface contamination, damage optical coatings, and damage bulk glass materials. In yet another example, multiple mechanisms are required (e.g., a spinning diffuser and scanning mirrors). Mechanisms increase the complexity of the system, increase the costs of parts, and are common failure points.

Accordingly, it would be advantageous to develop systems and methods for illuminating a specimen for inspection that use a coherent light source but illuminate the specimen with light that is not coherent and that provide ease of control over the distribution of light in the pupil of the systems, control over the distribution of light in the pupil without a substantial loss of light, a substantially uniform distribution of light in the field without losing a substantial amount of light, relatively low power densities on surfaces of optical components, a relatively simple configuration having relatively few mechanisms, or some combination thereof.

SUMMARY OF THE INVENTION

The following description of various system and method embodiments is not to be construed in any way as limiting the subject matter of the appended claims.

One embodiment relates to a system configured to provide illumination of a specimen for inspection. The system includes one or more first optical elements configured to illuminate a diffuser with a predetermined pattern of coherent light. The system also includes one or more second optical elements configured to image light exiting the diffuser onto an illumination pupil of the system such that the predetermined pattern is reproduced in the illumination pupil. In addition, the system includes an objective lens configured to focus light from the predetermined pattern in the illumination pupil onto a specimen plane.

In one embodiment, the system is configured to alter a position of the diffuser (e.g., by rotating, modulating, translating, or vibrating the diffuser) during the illumination of the specimen. In some embodiments, the one or more first optical elements include a diffractive optical element configured to generate the predetermined pattern of coherent light. In another embodiment, the one or more first optical elements include a diffractive optical element configured to generate the predetermined pattern of coherent light and to generate different patterns of coherent light that can be selected to illuminate the diffuser. In an additional embodiment, the one or more first optical elements include diffractive optical elements. Each of the diffractive optical elements is configured to illuminate the diffuser with a different pattern. The system is configured to position one of the diffractive optical elements in an optical path of the system based on the predetermined pattern and the different patterns of the diffractive optical elements.

In one embodiment, the system includes a homogenizer disposed in an optical path of the one or more second optical elements such that a distribution of the light exiting the diffuser is truncated at an entrance of the homogenizer. In some embodiments, the system includes a homogenizer disposed in an optical path of the one or more second optical elements, and the one or more second optical elements are configured to image a Fourier plane of the diffuser onto an entrance of the homogenizer. In another such embodiment, the system is configured to control at least one of the one or more second optical elements to alter a magnification of light exiting the homogenizer. In another embodiment, the system is configured to control one of the one or more first optical elements to alter a size of an area on the diffuser illuminated by the one or more first elements.

In some embodiments, the system includes a diffractive optical element and a homogenizer disposed in an optical path of the one or more second optical elements. The diffractive optical element is positioned at an image plane of the diffuser and is configured to distribute the light exiting the diffuser substantially uniformly at an entrance of the homogenizer. In a further embodiment, the system includes two or more homogenizers. The one or more second optical elements are configured to direct the light exiting the diffuser to the two or more homogenizers simultaneously and to direct light exiting the two or more homogenizers to the illumination pupil simultaneously. In some embodiments, the system includes a homogenizer disposed in an optical path of the one or more second optical elements, and the homogenizer includes a homogenizing rod, a homogenizing tunnel, or one or more arrays of lenses.

In some embodiments, the one or more first optical elements are configured to illuminate the diffuser with the predetermined pattern of coherent light at a first position and to illuminate the diffuser at a second position with light exiting the first position of the diffuser. The first and second positions are spatially separated across the diffuser. In a different embodiment, the system includes an additional diffuser. In such an embodiment, the one or more first optical elements are configured to illuminate the additional diffuser with the predetermined pattern of coherent light and to illuminate the diffuser with light exiting the additional diffuser in the predetermined pattern.

In one embodiment, the system includes a homogenizer disposed in an optical path of the one or more second optical elements and one or more polarizing components positioned downstream of the homogenizer in the optical path. In such an embodiment, the one or more polarizing components are configured to alter a polarization of the predetermined pattern of light. In some embodiments, the systems described herein may be configured to control one of the one or more second optical elements to alter a lateral position of the predetermined pattern in the illumination pupil. In another embodiment, the light focused onto the specimen plane is not substantially coherent. In one such embodiment, the system is configured to modulate the diffuser such that if an image of the specimen is generated (e.g., by an inspection system described herein), in the image the specimen appears to have been illuminated by incoherent light.

In a further embodiment, the predetermined pattern is selected based on an illumination mode selected for the inspection of the specimen. In another embodiment, the system includes a laser light source configured to direct coherent light having a wavelength below about 270 nm to the one or more first optical elements. In some embodiments, the coherent light includes multiple wavelengths of coherent light. In one such embodiment, the light focused from the predetermined pattern in the illumination pupil onto the specimen plane includes the multiple wavelengths of coherent light. In another such embodiment, the light focused from the predetermined pattern in the illumination pupil onto the specimen plane includes fewer than all of the multiple wavelengths of coherent light. In a further embodiment, the system includes a lamp light source. In one such embodiment, the system is configured to simultaneously focus light from the lamp light source and the light from the predetermined pattern in the illumination pupil onto the specimen plane. Each of the embodiments of the system described above may be further configured as described herein.

An additional embodiment relates to a system configured to inspect a specimen. The system includes one or more first optical elements configured to illuminate a diffuser with a predetermined pattern of coherent light. The system also includes one or more second optical elements configured to image light exiting the diffuser onto an illumination pupil of the system such that the predetermined pattern is reproduced in the illumination pupil. In addition, the system includes an objective lens configured to focus light from the predetermined pattern in the illumination pupil onto a specimen plane (e.g., at specific angles of incidence). The system further includes a detection subsystem configured to generate output signals responsive to light propagating from the specimen plane. The output signals can be used to detect defects on the specimen. The embodiment of the system described above may be further configured as described herein.

Another embodiment relates to a method for providing illumination of a specimen for inspection. The method includes illuminating a diffuser with a predetermined pattern of coherent light. The method also includes imaging light exiting the diffuser onto an illumination pupil such that the predetermined pattern is reproduced in the illumination pupil. In addition, the method includes focusing light from the predetermined pattern in the illumination pupil onto a specimen plane. The embodiment of the method described above may include any other step(s) described herein.

A further embodiment relates to a system configured to provide illumination of a specimen for inspection. This system includes one or more first optical elements configured to illuminate a diffuser with a predetermined pattern of low spatial coherence light. The system also includes one or more second optical elements configured to image light exiting the diffuser onto an illumination pupil of the system such that the predetermined pattern is reproduced in the illumination pupil. In addition, the system includes an objective lens configured to focus light from the predetermined pattern in the illumination pupil onto a specimen plane. In one embodiment, a position of the diffuser during the illumination is substantially stationary. This system embodiment may be further configured as described herein.

BRIEF DESCRIPTION OF THE DRAWINGS

Other objects and advantages of the invention will become apparent upon reading the following detailed description and upon reference to the accompanying drawings in which.

Figure 1:
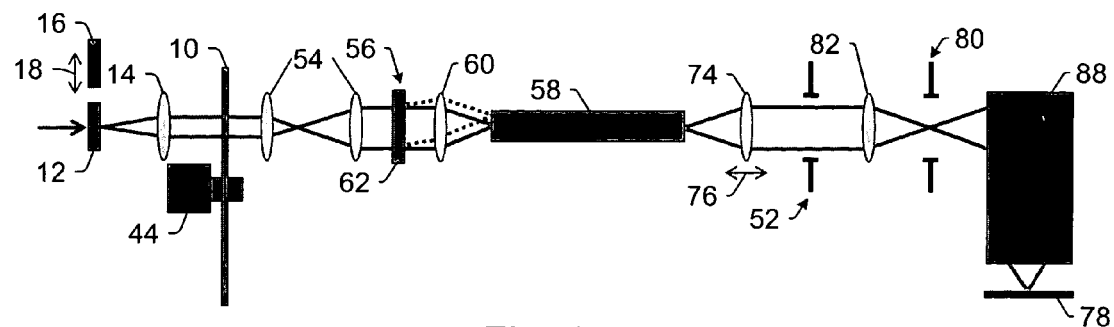
FIG. 1 is a schematic diagram illustrating a side view of one embodiment of a system configured to provide illumination of a specimen for inspection.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to provide illumination of a specimen for inspection. The system includes one or more first optical elements configured to illuminate diffuser 10 with a predetermined pattern of coherent light. In one embodiment, the one or more first optical elements include diffractive optical element 12. The one or more first optical elements may also include optical component 14. Optical component 14 may be configured to direct light exiting diffractive optical element 12 onto diffuser 10. In such an embodiment, diffuser 10 may be positioned at the Fourier transform plane of the diffractive optical element. Optical component 14 may include a refractive lens such as a spot lens or any other suitable optical component known in the art. In addition, although optical component 14 is shown as a single optical component in FIG. 1, it is to be understood that optical component 14 may include more than one optical component.

Diffractive optical element 12 is configured to generate the predetermined pattern of coherent light that illuminates the diffuser. In this manner, the diffractive optical element and optical component 14 establish the shape and size of the illuminated pattern on the diffuser. In particular, diffractive optical element 12 may be designed to diffract a laser beam such that the desired light distribution on the diffuser can be achieved. A diffractive optical element may be advantageously used to generate the predetermined pattern of coherent light that illuminates the diffuser since the diffractive optical element efficiently establishes the distribution of light that will eventually fill the system pupil. In some embodiments, if the system includes a homogenizer downstream of the diffuser, the area of the diffuser illuminated in the predetermined pattern may be left/right and up/down symmetric to prevent scrambling of the predetermined pattern of light by the homogenizer.

In one embodiment, diffractive optical element 12 may be a diffracting phase structure. In such an embodiment, the diffractive optical element may include a substantially flat element (e.g., a plate) formed of a substantially transparent material. A pattern may be printed on or etched into one surface of the substantially flat element. The pattern may be printed by forming a substantially opaque material on one surface of the substantially flat element and patterning the substantially opaque material using one or more processes such as lithography and/or etch. Lithography and/or etch may also be used to etch a pattern into the substantially flat element. In the case of a pattern etched into the substantially flat element, the etched portions of the element impart a phase pattern across the substantially flat element that controls diffraction of light from the substantially flat element. In this manner, the pattern that is formed on the substantially flat element determines diffraction of light by the diffractive optical element, which in turn determines the pattern in which coherent light illuminates the diffuser. In addition, diffractive optical element 12 may be an aperture, a spatial filter, or any other optical element that can be used to alter a pattern of light that exits the diffractive optical element. Furthermore, the diffractive optical element may have any other suitable configuration known in the art and may be formed using any suitable process or processes known in the art.

In some embodiments, the predetermined pattern of coherent light that illuminates the diffuser may include more than one beam of light that have predetermined characteristics such as shape, size, spacing between the more than one beam of light, and position across the optical path of the system. However, the predetermined pattern of coherent light that illuminates the diffuser more likely will include a single beam of light that has predetermined characteristics such as shape and size.

In some embodiments, the diffractive optical element may be configured to generate the predetermined pattern of coherent light and to generate different patterns of light that can be selected to illuminate the diffuser. For instance, if the diffractive optical element is a substantially flat element having a pattern formed thereon as described further above, then different portions of the diffractive optical element may have different patterns formed thereon. In this manner, the portion of the diffractive optical element that is positioned in the optical path of the system will determine the pattern of light that illuminates the diffuser. In one such embodiment, the system may be configured to alter a position of the diffractive optical element depending on the predetermined pattern of coherent light and the arrangement of the different patterns formed on the diffractive optical element. As such, the portion of the diffractive optical element that has a pattern that matches the predetermined pattern may be positioned in the optical path of the system. The system may be configured to alter the position of the diffractive optical element in the optical path using any method or apparatus known in the art.

In another embodiment, the one or more first optical elements include more than one diffractive optical element. For example, as shown in FIG. 1, the one or more first optical elements may include diffractive optical element 12 and diffractive optical element 16. Each of the diffractive optical elements is configured to illuminate the diffuser with a different pattern. As such, the light distribution on the diffuser can be changed by replacing diffractive optical element 12 with a different diffractive optical element (e.g., diffractive optical element 16) that has different diffractive properties. In one such embodiment, the system shown in FIG. 1 is configured to position one of the diffractive optical elements in an optical path of the system based on the predetermined pattern and the different patterns of the diffractive optical elements. In this manner, the diffractive optical element that has a pattern that matches the predetermined pattern may be positioned in the optical path of the system. The one or more diffractive optical elements may be moved into and out of the optical path by the system in the direction shown by arrow 18. However, the diffractive optical elements may be moved into and out of the optical path by the system in any other direction (e.g., by rotation). The system may be configured to move the diffractive optical elements into and out of the optical path of the system using any method or apparatus known in the art.

Figure 2:
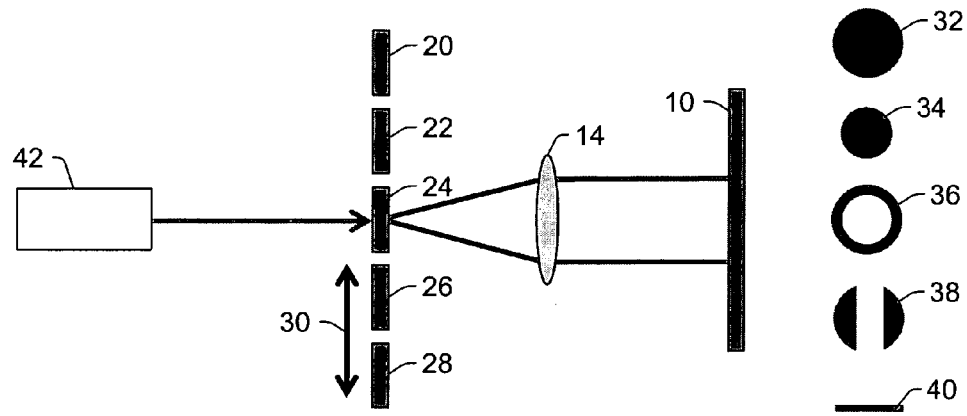
FIGS. 2-3 are schematic diagrams illustrating a side view of different embodiments of one or more first optical elements configured to illuminate a diffuser with a predetermined pattern of coherent light.

Although the one or more first optical elements are shown to include two diffractive optical elements in FIG. 1, the one or more first optical elements may include two or more diffractive optical elements. For example, as shown in FIG. 2, the one or more first optical elements may include diffractive optical elements 20, 22, 24, 26, and 28. Each of the diffractive optical elements may be configured to illuminate the diffuser with a different pattern. In this manner, the diffractive optical element that is positioned by the system in the optical path of the light may be selected based on the predetermined pattern and the diffractive optical element having a pattern that matches the predetermined pattern. The diffractive optical elements may be moved into and out of the optical path by the system in the direction indicated by arrow 30. However, these diffractive optical elements may be moved into and out of the optical path by the system as described further above.

Since each of the diffractive optical elements may be configured to illuminate the diffuser with a different pattern of light, each of the diffractive optical elements may produce a different distribution of light on the diffuser when positioned in the optical path. For instance, as shown in FIG. 2, diffractive optical element 20 may produce pattern 32 on diffuser 10 that is suitable for standard bright field inspection. Diffractive optical element 22 may produce pattern 34 on diffuser 10 that is suitable for low sigma (i.e., low partial coherence) inspection. Diffractive optical element 24 may produce pattern 36 on diffuser 10 that is suitable for standard Edge Contrast (which is a trademark of KLA-Tencor, San Jose, Calif.) inspection. Edge Contrast (EC) inspection generally uses a circular symmetric illumination aperture with a complementary imaging aperture. Diffractive optical element 26 may produce pattern 38 on diffuser 10 that is suitable for one-dimensional Fourier filtering inspection. Examples of one-dimensional Fourier filtering inspection methods and systems are illustrated in U.S. patent application Ser. No. _____ by Zhao et al., which is incorporated by reference as if fully set forth herein. Diffractive optical element 28 may produce pattern 40 on diffuser 10 that is suitable for Fourier filtering based inspection.

In this manner, the system may include interchangeable diffractive optical elements, each of which may be used for a different type of illumination and a different type of inspection. As such, the diffractive optical element positioned in the optical path of the system may be changed based on the selected illumination. In addition, in one embodiment, the predetermined pattern of coherent light that illuminates the diffuser is selected based on an illumination mode selected for the inspection of the specimen.

In the embodiments described herein, fine control of the shape of the light pattern on the diffuser is achieved using a diffractive optical element. However, other optical elements that can alter the shape of the light beam illuminating the diffuser may be used in place of such a diffractive optical element. For example, instead of a diffractive optical element and a transform lens, beam shaping lenses and apertures can be used to generate the predetermined pattern on the diffuser.

In the embodiments of the diffractive optical elements described above, the diffractive optical elements have one or more static (or unchanging) patterns formed thereon that can impart a pattern to a beam of light impinging thereon. However, in different embodiments, the first optical element (s) used to illuminate the diffuser with a predetermined pattern of coherent light may be configured such that the pattern generated by the optical element(s) is dynamic (i.e., can be altered). Although the patterns of light generated by the optical element(s) are dynamic, the same pattern may be imparted to a beam of light impinging thereon during an entire inspection process for a specimen.

In one such embodiment, the diffractive optical element described above and optical component 14 or another transform lens may be replaced with a programmable mirror array that can generate the predetermined pattern that illuminates the diffuser. The programmable mirror array may include a micro-mirror array such as one of the Digital Micromirror Devices (DMD) that are commercially available from Texas Instruments Incorporated, Dallas, Tex. Such a programmable mirror array may include an array of mirrors that extend across the entire optical path. Individual mirrors of the array may be turned off or on, for example, by flipping the individual mirrors into or out of position in the array. In this manner, the position of each of the individual mirrors in the array may be selected such that the array produces the predetermined pattern of coherent light that illuminates the diffuser. In such embodiment, the system may be configured to alter one or more properties of the programmable mirror array (e.g., which mirrors are turned off or on) depending on the predetermined pattern. In this manner, a relatively large number of different patterns (or "light distributions") may be programmed onto one optical element. The system may be configured to alter one or more properties of the optical element using any method or apparatus known in the art.

In another embodiment, the diffractive optical element may be replaced with a liquid crystal display (LCD) that can generate the predetermined pattern that illuminates the diffuser. In this manner, individual "segments" of the LCD may be controlled to be either substantially transparent or substantially opaque to the light that is passing through the LCD. For instance, a voltage applied to the individual segments may vary depending on whether the segment is turned on or off. In this manner, the individual segments of the LCD may be controlled such that light exits the LCD in the predetermined pattern. In this manner, a relatively large number of different patterns (or "light distributions") may be programmed onto one optical element. Such control of the individual segments of the LCD may be performed by the systems described herein using any method or device known in the art.

Light illuminating the diffractive optical element (or an optical element used in place of the diffractive optical element) includes coherent light. For example, in one embodiment shown in FIG. 2, the system includes light source 42. Light source 42 is configured to generate coherent light. One example of a coherent light source is a laser light source. The coherent light source may also be a continuous-wave (cw) laser or a mode-locked laser. The laser light source may be configured to generate light having any suitable wavelength or wavelengths known in the art such as visible, ultraviolet (UV), deep ultraviolet (DUV), near vacuum ultraviolet (near-VUV), VUV, or some combination thereof. In one embodiment, the laser light source may be configured to direct light having a wavelength below about 270 nm to the one or more first optical elements. However, the wavelength(s) of the light emitted by the light source may be selected based on, for example, one or more characteristics of the specimen, one or more characteristics of the defects of interest, and one or more characteristics of other optical components of the system. The systems described herein may, therefore, be configured for narrow band (NB) illumination inspection. In some embodiments, the coherent light includes multiple wavelengths of coherent light. The portion of the system shown in FIG. 2 may be included in any of the system embodiments described herein. In addition, the portion of the system shown in FIG. 2 may be further configured as described herein.

Since the one or more first optical elements (e.g., diffractive optical element 12 and optical component 14) are not configured to alter the coherence of the light from the light source, the diffuser is illuminated with a coherent laser beam in a predetermined pattern. In one embodiment, the system is configured to alter a position of diffuser 10 during illumination of the specimen. For example, the system may be configured to rotate, modulate, translate, or vibrate the diffuser during the illumination of the specimen. In this manner, the system may be configured to alter a position of diffuser 10 during the integration time of the sensor (not shown in FIG. 1) used for inspection. Altering a position of diffuser 10 during the integration time of the sensor scatters the light and modulates speckle over the integration time. As such, speckle introduced by the diffusion of the laser beam may be modulated such that the speckle contrast in the image of the specimen generated during inspection is reduced over the integration time of the sensor. In other words, unlike a stationary diffuser that will produce a speckle pattern in images of the specimen, altering a position of the diffuser may "average" the speckle pattern over the integration time of the sensor. The sensor may be configured as described herein.

In one such embodiment, diffuser 10 may be coupled to motor 44. Motor 44 may include any suitable device known in the art. Motor 44 may be configured to rotate the diffuser at a selectable rotations per minute (rpm). Motor 44 may be controlled by the system. In particular, the system may be coupled to motor 44 by any method or device known in the art such that the system may control the speed at which diffuser 10 is rotated.

In other embodiments, however, a position of the diffuser during the illumination is substantially stationary. For example, instead of illuminating the diffuser with a predetermined pattern of coherent light, the one or more first optical elements may be configured to illuminate the diffuser with a predetermined pattern of low spatial coherence light. In one such example, the coherent light source of the system may be replaced with a substantially bright, incoherent light source such as a laser light source that produces a laser beam having low spatial coherence. In this manner, the diffuser would not introduce speckle into the illumination. As such, altering the position of the diffuser to reduce the speckle may be eliminated. Such an embodiment of the system may be further configured as described herein.

As shown in FIG. 1, the light exiting collection lens 14 illuminates diffuser 10 once with the predetermined pattern of coherent light. However, in other embodiments, the predetermined pattern of coherent light may be passed through diffuser 10 more than once. For example, in one embodiment, the one or more first optical elements (e.g., diffractive optical element 12 and optical component 14) are configured to illuminate diffuser 10 with a predetermined pattern of coherent light at a first position. In such an embodiment, the one or more first optical elements are configured to illuminate the diffuser at a second position with light exiting the first position of the diffuser. The first and second positions are spatially separated across the diffuser. In this manner, the predetermined pattern of coherent light may be passed through a single diffuser more than once. An embodiment of a system including such an embodiment of one or more first optical elements and a diffuser is described further herein.

Figure 3:
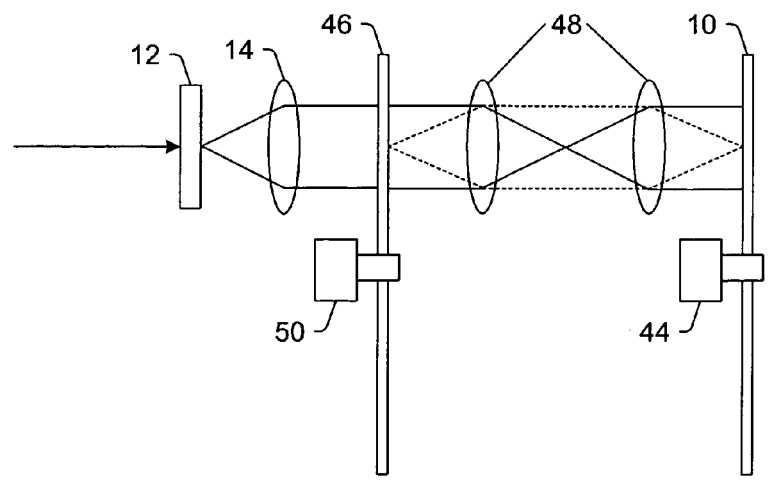

In an alternative embodiment, the system may include additional diffuser 46 shown in FIG. 3. In this embodiment, the one or more first optical elements (e.g., diffractive optical element 12 and optical component 14) are configured to illuminate additional diffuser 46 with the predetermined patterned of coherent light. In addition, the one or more first optical elements are configured to illuminate diffuser 10 with light exiting additional diffuser 46 in the predetermined pattern. For instance, the one or more first optical elements may include optical element 48. Optical element 48 is configured to image light exiting additional diffuser 46 onto diffuser 10.

As shown in FIG. 3, optical element 48 may include two lenses. The lenses may be refractive lenses or any other lenses known in the art. Although optical element 48 is shown in FIG. 3 to include two lenses, it is to be understood that this optical element may include one or more lenses. Two lenses used in optical element 48 may be suitable for the embodiment shown in FIG. 3 in which one of the two lenses collects light exiting additional diffuser 46 and the second of the two lenses images the light collected by the first lens onto diffuser 10.

In some such embodiments, the system is configured to alter a position of additional diffuser 46 during illumination of the specimen. For example, the system may be configured to rotate, modulate, translate, or vibrate additional diffuser 46 during illumination of the system. In this manner, the system may be configured to alter a position of additional diffuser 46 during the integration time of the sensor (not shown in FIG. 3) used for inspection. As such, speckle introduced by the diffusion of the laser beam may be modulated such that the speckle contrast in the image of the specimen generated during inspection is reduced over the integration time of the sensor. In other words, unlike a stationary diffuser that will produce a speckle pattern in images of the specimen, altering a position of the diffuser may "average" the speckle pattern over the integration time of the sensor. The sensor may be configured as described herein.

In one such embodiment, additional diffuser 46 may be coupled to motor 50. Motor 50 may include any suitable device known in the art. Motor 50 may be configured to rotate the diffuser at a selectable rpm. Motor 50 may be controlled by the system as described above. In addition, additional diffuser 46 and diffuser 10 may be rotated at the same speed or different speeds during illumination of the specimen.

Diffuser 10 and additional diffuser 46 may be configured similarly or differently. In addition, diffuser 10 and additional diffuser 46 may be any suitable diffusers known in the art. For example, the diffusers may be ground glass diffusers. A ground glass diffuser randomly scatters the incident light over a predictable angular distribution. In another example, the diffusers may be "programmed" or printed diffusers instead of ground glass diffusers. Unlike typical diffusers that scatter light in a Gaussian manner, a programmed or printed diffuser may be configured to generate pseudo-random diffraction of light incident thereon. The diffusers described above are transmissive type diffusers. However, the diffusers may be reflective diffusers. A reflective diffuser may include a metal pattern formed on a glass substrate. In addition, the reflective diffuser may include any other suitable reflective diffuser known in the art. The portion of the system shown in FIG. 3 may be included in any of the system embodiments described herein. In addition, the portion of the system shown in FIG. 3 may be further configured as described herein.

The number of times that the light passes through a single diffuser or the number of diffusers through which the light is passed may vary depending on, for example, the ability of the individual diffusers to reduce speckle noise in the illumination. For instance, it may be possible to sufficiently reduce speckle noise using a single ground glass diffuser. However, speckle noise may be further reduced by passing the light through multiple diffusing elements. In addition, as described further above, the systems described herein are compatible with using more than one diffusing surface. For instance, as described further above, the first diffuser surface is imaged onto the second diffuser surface. In such instances, the light exiting the second diffuser surface is eventually imaged into the system illumination pupil as described further herein. As described above, more than one diffusing surface may be provided by passing light through the same diffuser at least twice or by passing light through at least two different diffusers. However, imaging the light back through a single diffuser is advantageous in that the part count of the system is lower.

The system also includes one or more second optical elements configured to image light exiting the diffuser onto illumination pupil 52 of the system such that the predetermined pattern is reproduced in the illumination pupil. As such, unlike previously used systems configured to illuminate a specimen for inspection that image a diffuser onto an entrance of a homogenizer, the diffuser surface is imaged into the system pupil. In this manner, the predetermined pattern of light illuminating the diffuser is reproduced in the illumination pupil of the system. The shape of the light pattern formed on the diffuser thereby defines the light distribution in the system pupil. As such, light can be efficiently distributed to only the desired areas of the system pupil. In this manner, the system may be configured to distribute the light over desired areas of the system pupil while minimizing the light falling outside of the desired areas. For instance, as described further above, a diffractive optical element can be used to efficiently generate arbitrary light distributions on the diffuser and thereby in the system pupil. Therefore, modifying or altering the predetermined pattern of coherent light that illuminates the diffuser effectively modifies or alters the distribution of light in the illumination pupil of the system. For example, as described above, the distribution of the coherent light illuminating the diffuser can be easily modified by changing the diffractive optical element that is positioned in the optical path of the system. In this manner, the distribution of the light in the system pupil can also be easily modified by changing the diffractive optical element that is positioned in the optical path of the system. As such, the systems described herein provide control over the area of the pupil that is illuminated.

In one embodiment, the one or more second optical elements include collection lens 54. As shown in FIG. 1, collection lens 54 may include two lenses. The lenses may be refractive lenses or any other lenses known in the art. Although collection lens 54 is shown in FIG. 1 to include two lenses, it is to be understood that the collection lens may include one or more lenses. A collection lens that includes two lenses may be suitable for the embodiment shown in FIG. 1 in which one of the two lenses collects light exiting the diffuser and the second of the two lenses images the light collected by the first lens to image plane 56.

As shown in FIG. 1, homogenizer 58 may be disposed in an optical path of the one or more second optical components. Homogenizer 58 is configured to increase the uniformity of the field illumination. The system is configured such that the scatter distribution from diffuser 10 is imaged into an entrance of homogenizer 58. In some embodiments, the homogenizer may be disposed in the optical path of the one or more second optical elements such that a distribution of the light exiting the diffuser is truncated at an entrance of the homogenizer. In another embodiment, the one or more second optical elements are configured to image a Fourier plane of diffuser 10 onto an entrance of the homogenizer. In one such embodiment, the one or more second optical elements may include fill lens 60. Fill lens 60 is configured to direct light from image plane 56 to the entrance of the homogenizer. As shown in FIG. 1, fill lens 60 may be configured as a refractive lens. Alternatively, fill lens 60 may be configured as a reflective optical element.

In an additional embodiment, the system includes diffractive optical element 62 disposed in an optical path of the one or more second optical elements. Diffractive optical element 62 is positioned at image plane 56 of diffuser 10. In this manner, the diffuser surface may be imaged onto an additional diffractive optical element. Diffractive optical element 62 is configured to distribute the light exiting the diffuser substantially uniformly at an entrance of homogenizer 58. For instance, diffractive optical element 62 may diffract the beam of light from the diffuser so that the light distribution at its Fourier transform plane efficiently and uniformly fills the entrance of the homogenizer.

Figure 4:
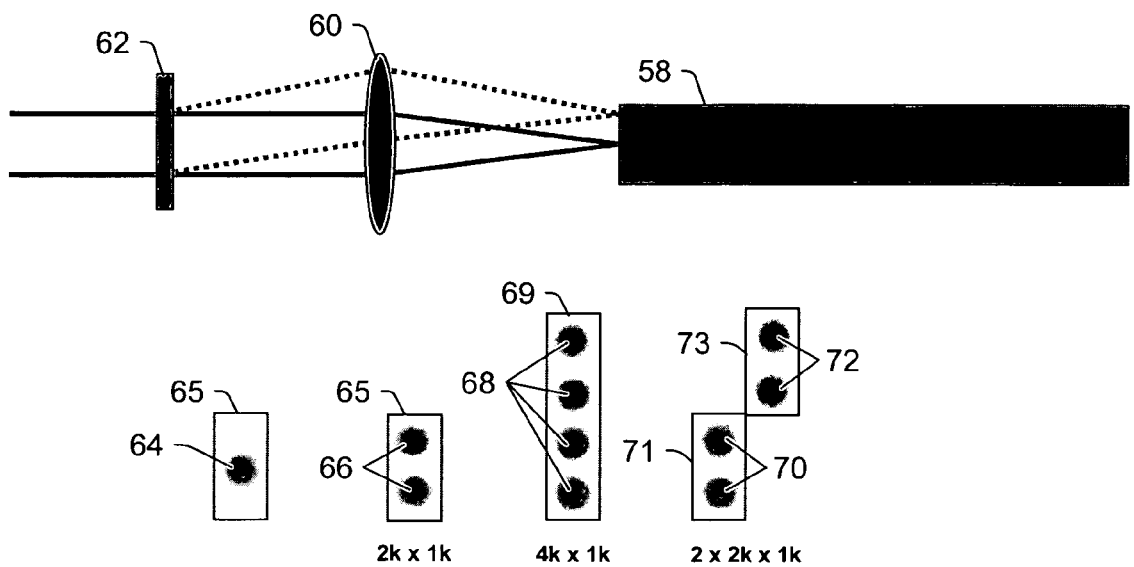
FIG. 4 is a schematic diagram illustrating a side view of one embodiment of a diffractive optical element and a homogenizer that may be disposed in an optical path of one or more second optical elements of the system embodiments described herein.

In particular, as shown in FIG. 4, light from the diffuser (not shown in FIG. 4) may be imaged onto diffractive optical element 62. In particular, as shown in FIG. 1, collection lens 54 collects the scattered light from diffuser 10 and forms an image of the surface of the diffuser on diffractive optical element 62. Light from diffractive optical element 62 is directed to the entrance of homogenizer 58 by fill lens 60. Diffractive optical element 62 and fill lens 60 diffract the light so that it more uniformly fills the entrance of the homogenizer. In this manner, the light distribution at the entrance of the homogenizer may vary depending on the configuration of diffractive optical element 62.

For instance, as shown in FIG. 4, light distribution 64 will illuminate entrance 65 of the homogenizer if diffractive optical element 62 is not included in the system. As shown by light distribution 64 on entrance 65, a substantial portion of the entrance of the homogenizer is not illuminated by the light from the diffuser. As shown in FIG. 4, the homogenizer may have a rectangular cross-sectional area. In this manner, the homogenizer will truncate the Gaussian scatter distribution from diffuser 10 differently in the x and y directions. A more uniform fill of the entrance of the homogenizer is generally preferred to improve uniformity in the illumination pupil.

In contrast, light distribution 66 will illuminate entrance 65 of the homogenizer when one embodiment of diffractive optical element 62 is included in the system. As shown by comparison of light distributions 64 and 66, by positioning a diffractive optical element at an imaging plane of the diffuser, a much larger portion of the entrance of the homogenizer is illuminated by the light from the diffuser. A more complex diffractive optical element can produce even better uniformity than that illustrated in distribution 66. In addition, the configuration of the diffractive optical element may vary depending on the configuration of the imaging sensor (not shown in FIG. 4) that is used with the illumination systems described herein. The imaging sensor may be configured as described further herein. For instance, light distribution 66 may be suitable for an imaging sensor that includes a 2,000×1,000 array of pixels. However, for a larger imaging sensor (e.g., an imaging sensor that includes a 4,000×1,000 array of pixels), a homogenizer having a larger cross-sectional area may be included in the system. As such, diffractive optical element 62 may be configured to produce light distribution 68 at entrance 69 of the homogenizer. In this manner, the light distribution may be relatively uniform across the entrance of the homogenizer even though the homogenizer has a substantial length in one direction.

In some embodiments, the system may include two or more homogenizers. The two or more homogenizers may be similarly configured. In one such embodiment, the one or more second optical elements are configured to direct light exiting the diffuser to the two or more homogenizers simultaneously. For example, as shown in FIG. 4, diffractive optical element 62 may be configured to generate light distribution 70 at the entrance of homogenizer 71 and light distribution 72 at the entrance of homogenizer 73. In this manner, the diffractive optical element positioned at the image plane of the diffuser can be designed to simultaneously illuminate the entrance of more than one homogenizer.

As further shown in FIG. 4, the entrances of the homogenizers may be offset from one another in both the x and y directions. In some such embodiments, the one or more second optical elements are configured to direct light exiting the two or more homogenizers to illumination pupil 52 (shown in FIG. 1) simultaneously. In this manner, more than one homogenizer can be used to illuminate more than one area on the specimen. Such a configuration of two or more homogenizers may be suitable for a system that includes two or more imaging sensors, each of which includes a 2,000× 1,000 array of pixels. Such a configuration may advantageously increase the throughput of an inspection system in which the illumination system is included since a larger area on the specimen may be illuminated and imaged simultaneously. In addition, the number of homogenizers included in the system may include one or more and may in some instances be equal to the number of imaging sensors included in the system.

Accordingly, a diffractive optical element may be inserted at an image plane of the diffuser surface to improve the uniformity of light distribution at the entrance of the homogenizer. Such a diffractive optical element may be further configured as described above with respect to diffractive optical element 12. In addition, other optical components may be used to distribute the light exiting the diffuser substantially uniformly at the entrance of the homogenizer. For instance, anamorphic or cylindrical optics can be used instead of a diffractive optical element to increase light uniformity at the entrance to the homogenizer. In one such example, fill lens 60 may be configured as an anamorphic optical element to increase the uniformity of the light distribution on the entrance of the homogenizer. However, a diffractive optical element design is less complex than anamorphic lenses and provides greater flexibility and adaptability to different homogenizer sizes and configurations.

The exit of the homogenizer is eventually imaged on the specimen as described further herein. In one embodiment, homogenizer 58 includes a homogenizing rod. The cross-sectional dimensions of the homogenizing rod may be selected so that the image of the homogenizing rod that is formed on a specimen as described further herein closely matches the field of view of the imaging sensor. In addition, the length of the homogenizing rod may be selected to provide a number of bounces that can produce the desired degree of light uniformity at its exit. In another embodiment, homogenizer 58 includes a homogenizing tunnel that may be further configured as described herein. Unlike a homogenizing rod that generally has a rectangular or hexagonal cross-section, a homogenizing tunnel generally includes a number of mirrors (e.g., four) assembled to form a hollow center. The homogenizing rod and the homogenizing tunnel may include any suitable components known in the art.

The one or more second optical elements may also include one or more optical elements that are configured to collect light exiting the homogenizer. For example, as shown in FIG. 1, the one or more second optical elements may include pupil lens 74. Pupil lens 74 may be configured to collect light exiting the homogenizer. Pupil lens 74 may also be configured to image the surface of the diffuser to illumination pupil 52. As shown in FIG. 1, pupil lens 74 may be a refractive optical element. However, the pupil lens may alternatively be a reflective optical element. The pupil lens may include any suitable optical element known in the art.

In one embodiment, the system is configured to control at least one of the one or more second optical elements to alter a magnification of the light exiting the homogenizer. For instance, in one embodiment, pupil lens 74 may also be used as a zooming optical element. In particular, pupil lens 74 may be configured to adjust the magnification of the light exiting homogenizer 58 at field stop 80. In one such example, the system may be coupled to pupil lens 74 such that the system can move the pupil lens in directions indicated by arrow 76. As such, the system may be configured to physically change the focal length of the system. The focal length of the pupil lens can be altered depending on the selected magnification of the system.

In one embodiment, the pupil lens position may be altered to change the size of the illuminated field of view on specimen 78. In this manner, the size of the illuminated area of specimen 78 can be easily modified by changing the magnification from the homogenizing rod exit to the specimen. In addition, the magnification from the homogenizer to the specimen may be adjusted such that the size of the illuminated area on the specimen matches the field of view of the imaging sensor. The imaging sensor may be configured as described further herein. In this manner, the magnification from the homogenizer to specimen 78 may be adjusted to minimize the amount of light that falls outside of a field of view of an imaging sensor. As such, the homogenizer in combination with pupil lens 74 may be used to uniformly distribute light over an intended field of view while minimizing the light falling outside of this field. Therefore, light may be efficiently and uniformly distributed over the field of view of the imaging sensor.

In another embodiment, the system invariant may be altered by reducing the size of the illuminated area on diffuser 10 while zooming the magnification to field stop 80. In one such embodiment, the system may be configured to control one of the one or more first optical elements to alter a size of an area on diffuser 10 illuminated by the one or more first optical elements. The system may be configured to control diffractive optical element 12 and/or optical component 14 to alter the size of the area on the diffuser that is illuminated by the one or more first optical elements. The system may be configured to control diffractive optical element 12 as described above such that the predetermined pattern of light illuminates a smaller cross-sectional area of the diffuser. Alternatively, the system may be configured to control optical component 14 by altering a position of this optical component along the optical path of the system. The system may be configured to use any method or device known in the art to alter the position of optical component 14.

As described above, therefore, the system may be configured to diffuse the laser beam so that the field of view of the imaging sensor is illuminated and an extended area of the system pupil is illuminated. The extended area of the system pupil that is illuminated may be greater than a point of light. For example, the extended area of the system pupil that is illuminated may include substantially the entire system pupil. In addition, the power densities of the light on the specimen and the objective lens of the optical system may be minimized since both the system pupil and the field of view can be fully illuminated at all times during the image acquisition. The systems described herein are also advantageous in that only one mechanism, the rotating or otherwise moving diffuser, is used to break up the spatial coherence of the laser illumination during the image acquisition.

The one or more second optical elements may also include field lens 82. Field lens 82 may be configured to focus light from illumination pupil 52 to field stop 80. The field lens may include any appropriate refractive lenses or reflective lenses known in the art. Objective lens 88 is configured to focus light from the predetermined pattern in illumination pupil 52 onto specimen plane 78. For example, the objective lens may be configured to direct light from the predetermined pattern in illumination pupil 52 into specific angles at specimen plane 78. As described above, the predetermined pattern of light illuminating the diffuser includes coherent light. However, motion in the diffuser modulates the speckle pattern so that the illumination of the specimen plane appears to be substantially incoherent over the integration time of the imaging sensor. In other words, the light focused onto the specimen plane is not substantially coherent. In this manner, the illumination systems described herein may utilize a coherent laser light source to provide illumination for generating incoherent or partially coherent images of a specimen such as a semiconductor wafer or photomask.

As described above, the coherent light may include multiple wavelengths of coherent light. In one such embodiment, the light focused from the predetermined pattern in the illumination pupil onto the specimen plane includes the multiple wavelengths of coherent light. In this manner, the specimen may be illuminated with the multiple wavelengths of coherent light simultaneously. In another embodiment, the light focused from the predetermined pattern in the illumination pupil onto the specimen plane includes fewer than all of the multiple wavelengths of coherent light. In this manner, the specimen may be illuminated with fewer than all of the multiple wavelengths of coherent light simultaneously. In addition, the system may be configured to illuminate the specimen with one or more of the multiple wavelengths of light individually. For example, the system may be configured to illuminate the specimen with selected wavelengths individually and sequentially (e.g., one wavelength at a time).

Such illumination systems provide a number of advantages over illumination systems that generate coherent images of a specimen. For example, an image generated using coherent illumination may include artifacts such as ringing while using non-coherent light to illuminate a specimen substantially eliminates ringing in images of the specimen. In addition, images that do not have such artifacts do not have to be aligned as precisely for image comparison. Furthermore, eliminating such artifacts from images generated by an inspection system increases the resolution of the inspection system.

The illumination system shown in FIG. 1 may be utilized in any existing inspection system. For instance, an existing inspection system may be retrofitted to include an embodiment of an illumination system described herein. The illumination system may replace the existing illumination system used in the inspection system or may be used as an additional illumination system. The illumination system may include a laser light source as described further above. The illumination system may, however, be configured to provide laser and other illumination (e.g., broad band or lamp illumination) both independently and simultaneously. For instance, light from a broad band or lamp light source (not shown) may be introduced into the optical path of the illumination system shown in FIG. 1 downstream of homogenizer 58 using one or more optical elements (not shown) such as a polarizing beam splitter, a dichroic beam splitter, or a reflective optical component that is configured to be moved into and out of the illumination path. In one such embodiment, the system also includes a lamp light source. In such an embodiment, the system may be configured to simultaneously focus light from the lamp light source and the light from the predetermined pattern in the illumination pupil onto the specimen plane. The system shown in FIG. 1 may be further configured as described herein.

As is evident from the description of FIG. 1 and other figures presented herein, one advantage of the illumination systems described herein is that the illumination systems can be used for a variety of inspection modes. Therefore, the illumination systems can be used to provide a number of different inspection modes in a single inspection system. These different inspection modes include, but are not limited to, bright field, low sigma bright field, EC, one-dimensional Fourier filtering, directional dark field, phase contrast, polarization, single-line Fourier filtering, or some combination thereof.

Figure 5:
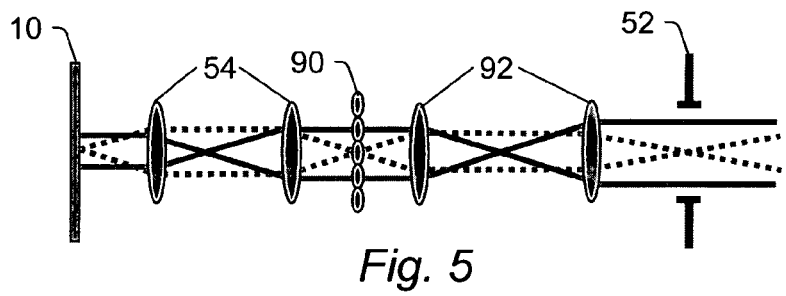
FIGS. 5-6 are schematic diagrams illustrating a side view of various embodiments of one or more second optical elements configured to image light exiting a diffuser onto an illumination pupil such that the predetermined pattern is reproduced in the illumination pupil.

As described above, a homogenizer such as a homogenizing rod or a homogenizing tunnel may be included in the illumination system to increase the uniformity of the illumination across the field of view of the system. However, in other embodiments, one or more arrays of lenses can be used as a homogenizer instead of a homogenizing rod or tunnel to improve the uniformity of the light distribution on the specimen. One such embodiment is illustrated in FIG. 5. In particular, FIG. 5 illustrates one embodiment of one or more second optical elements configured to image light exiting a diffuser onto an illumination pupil such that the predetermined pattern is reproduced in the illumination pupil. As shown in FIG. 5, light exiting diffuser 10 is directed to collection lens 54. Diffuser 10 and collection lens 54 may be configured as described herein. Light exiting collection lens 54, in this embodiment, is directed to single lens array 90. Single lens array 90 is configured to increase the uniformity of the illumination across the field of view of the system. Single lens array 90 may be positioned at an image plane of the diffuser.

As shown in FIG. 5, the single lens array may include five lenses across one dimension of the single lens array. In addition, although not shown in FIG. 5, the single lens array may include a two-dimensional array of lenses. The lenses of the single lens array may include refractive optical elements. In addition, each of the lenses of the single lens array may be similarly configured. Each of the lenses may be spherical lenses or lenses having one flat surface and one curved or aspheric surface. Furthermore, the single lens array may include any suitable number of lenses across both dimensions of the single lens array. The single lens array may also include any suitable lens array known in the art such as a lenslet array, a fly's eye lens array, etc.

As further shown in FIG. 5, the one or more second optical elements may include collection lens 92. Collection lens 92 is configured to collect light exiting the single lens array and to image the collected light to illumination pupil 52. Illumination pupil 52 may be positioned at an image plane of single lens array 90. As shown in FIG. 5, collection lens 92 may include two lenses. The lenses may be refractive lenses or any other lenses known in the art. Although collection lens 92 is shown in FIG. 5 to include two lenses, it is to be understood that the collection lens may include one or more lenses. Two lenses used in collection lens 92 may be suitable for the embodiment shown in FIG. 5 in which one of the two lenses collects light exiting the single lens array and the second of the two lenses images the light collected by the first lens to illumination pupil 52. The one or more second optical elements shown in FIG. 5 may be included in any of the system embodiments described herein.

Figure 6:
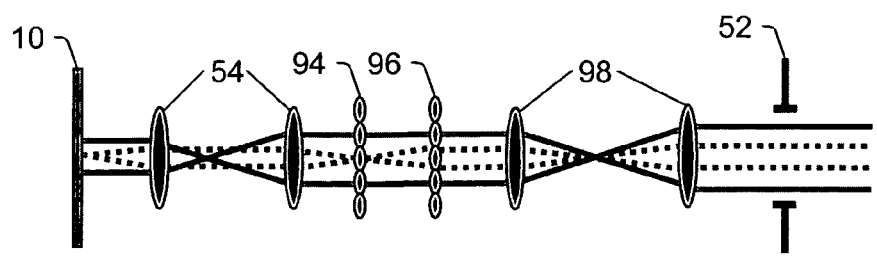

FIG. 6 illustrates a different embodiment of one or more second optical elements configured to image light exiting a diffuser onto an illumination pupil such that the predetermined pattern is reproduced in the illumination pupil. As shown in FIG. 6, light exiting diffuser 10 is directed to collection lens 54. Diffuser 10 and collection lens 54 may be configured as described herein. Light exiting collection lens 54, in this embodiment, is directed to lens array 94. Light exiting lens array 94 is directed to lens array 96. In this manner, the embodiment shown in FIG. 6 includes two lens arrays that are spatially separated from one another along the illumination path of the one or more second optical elements. Lens arrays 94 and 96 are configured to increase the uniformity of the illumination across the field of view of the system. Lens array 94 may be positioned at an image plane of the diffuser. Lens array 96 may be positioned at a conjugate plane of illumination pupil 52.

As shown in FIG. 6, the lens arrays may include five lenses across one dimension of the lens arrays. In addition, although not shown in FIG. 6, the lens arrays may include two-dimensional arrays of lenses. The lenses of the lens arrays may include refractive optical elements. In addition, each of the lenses of the lens arrays may be similarly configured. Furthermore, the lens arrays may include any suitable number of lenses across both dimensions of the lens arrays. Moreover, although the embodiment of FIG. 6 is shown to include two lens arrays, it is to be understood that the embodiments described herein may include more than two lens arrays that are configured to increase the uniformity of the illumination across the field of view of the system.

As further shown in FIG. 6, the one or more second optical elements may include collection lens 98. Collection lens 98 may be configured to collect light exiting lens array 96 and to image the collected light to illumination pupil 52. Illumination pupil 52 may be positioned at an image plane of lens array 96. As shown in FIG. 6, collection lens 98 may include two lenses. The lenses may be refractive lenses or any other lenses known in the art. Although collection lens 98 is shown in FIG. 6 to include two lenses, it is to be understood that the collection lens may include one or more lenses. A collection lens that includes two lenses may be suitable for the embodiment shown in FIG. 6 in which one of the two lenses collects light exiting lens array 96 and the second of the two lenses images the light collected by the first lens to illumination pupil 52. The one or more second optical elements shown in FIG. 6 may be included in any of the system embodiments described herein.

In systems that include the one or more second optical elements shown in FIGS. 5 and 6, the etendue of the system may be altered by changing the size of the individual lenses in the lens array(s) without altering the focal lengths of the lenses. Changing the etendue of the system in this manner is analogous to changing the cross section of a homogenizing rod. In one such embodiment, the system may include different lens array(s) that include individual lenses having different sizes. In this manner, depending on the selected etendue, the system may alter the lens array(s) that is/are positioned in the illumination path of the system. The system may alter the lens array(s) that is/are positioned in the illumination path using any appropriate method or device known in the art.

In a different embodiment, the Fourier transform plane of the diffuser can be imaged directly onto the specimen without passing through any of the homogenizers or arrays of lenses described above. Therefore, the system may have a simpler and less expensive optical design.

Figures 7, 8:
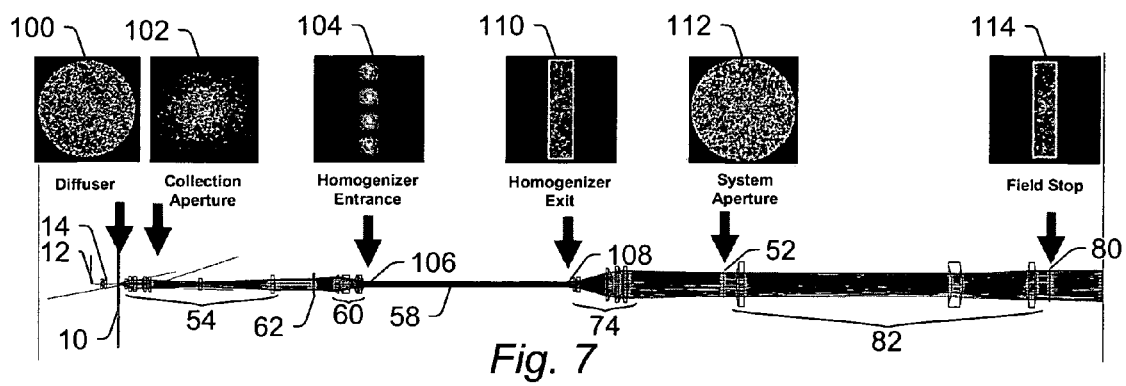
FIG. 7 includes a ray trace simulated for one embodiment of a system configured to provide illumination of a specimen for inspection and simulated light distributions at various points in the system.
FIG. 8 includes simulated light distributions at various points in the system illustrated in FIG. 7 using a different predetermined pattern of light to illuminate the diffuser and different magnifications of light exiting a homogenizer.

FIG. 7 illustrates a ray trace simulated for one embodiment of a system configured to provide illumination of a specimen for inspection and simulated light distributions at various points in the embodiment of the system. Elements shown in FIG. 7 using the same reference numerals shown in FIG. 1 may be configured as described herein with respect to FIG. 1. The simulations were performed using a non-sequential ray trace model. In this simulation, more than 100,000 random, incoherent rays are traced. (No interference effects were considered.) In addition, the optical design of the system for which the simulated light distributions were generated was selected to include 22 fused silica lenses from diffractive optical element 12 to field stop 80. In this optical design, homogenizer 58 was selected to have dimensions of 3.7 mm×0.9 mm×150 mm for an application in which a time delay integration (TDI) sensor (not shown in FIG. 7) that includes 4000 pixels×1000 pixels will be used as the detector. This optical design has a total track length of 784 mm.

The simulations were performed for a point light source (not shown) configured to illuminate diffractive optical element 12. Diffractive optical element 12 was simulated as an aperture that illuminates diffuser 10 with predetermined pattern of light 100 (i.e., the illumination patch on the diffuser). Diffuser 10 was simulated as a ground glass diffuser. The diffuser produces light distribution 102 at the collection aperture of the system. Light distribution 102 illustrates that the diffuser scatters light randomly in a Gaussian distribution with $1/e^2$ at a numerical aperture (NA) of 0.45.

As described further above, the Gaussian scatter distribution of the diffuser is truncated at the entrance of the homogenizer instead of at the system pupil as in previously used illumination systems. Truncating the scatter distribution at the entrance of the homogenizer instead of at the system pupil provides a number of advantages over previously used illumination systems. For instance, when truncating the Gaussian scatter distribution at the system pupil, in order to conserve light and maximize speckle reduction, the Gaussian scatter distribution may be truncated at the $1/e^2$ point in the illumination pupil. This truncation results in an effective partial coherence for the inspection system that is less than one. In addition, the truncation at the illumination pupil will produce a steep pupil roll-off (i.e., a substantial decrease in illumination power density across the radius of the illumination pupil proximate the edges of the illumination pupil) that will be very inefficient for certain aperture modes of inspection such as EC inspection modes.

In contrast, truncating the Gaussian scatter distribution of the diffuser at the entrance of the homogenizer will not produce field non-uniformity or pupil roll-off. In addition, truncating the Gaussian scatter distribution of the diffuser at the entrance of the homogenizer will produce a light distribution at the illumination pupil that has some structure or predetermined pattern. In this manner, by imaging the diffuser into the system pupil instead of the entrance of the homogenizer, the opportunity for utilizing "engineered" pupil fills becomes available. Furthermore, by imaging the diffuser into the system pupil, the light can be efficiently directed to any desired area of the system pupil by changing the shape of the illumination spot on the diffuser. In this manner, if an inspection mode utilizes some obscuration, substantially no light will be lost due to the obscuration since the light can be efficiently mapped to the utilized portions of the illumination pupil. The degree of truncation can be selected to balance pupil structure, light efficiency, and the diffuser's decorrelation distance.

Diffractive optical element 62 in this example was modeled as a diffraction grating. Diffractive optical element 62 may be further configured as described herein. Diffractive optical element 62 produces light distribution 104 at entrance 106 of homogenizer 58. As shown by light distribution 104, diffractive optical element 62 produces a much more uniform distribution of light across entrance 106 of homogenizer 58 than if a single beam of light was directed to the entrance of homogenizer 58. Such an increase in the uniformity of the light distribution at the entrance of the homogenizer is advantageous since each point in the field of the system will "see" the pupil structure depending on the light distribution at the homogenizer entrance.

Light at exit 108 of homogenizer 58 has light distribution 110. Light at illumination pupil 52 (or system aperture) has light distribution 112. As shown by comparison of light distribution 100 of the illumination patch on the diffuser and light distribution 112 at illumination pupil 52, a sharp image of the illumination patch on the diffuser is formed at the illumination pupil. In addition, the total light distribution at illumination pupil 52 is highly uniform. Therefore, the risk of coating damage of the objective lens of the system due to the distribution of light at the illumination pupil is negligible. Such reduction in the risk of coating damage to the objective lens is advantageous since it allows higher power light sources to be used for inspection applications. Higher power light sources are particularly advantageous for a number of inspection modes such as broad band bright field inspection at relatively small pixel sizes (e.g., pixel sizes of 90 nm), DUV bright field, and inspection modes that utilize some restriction or obscuration of the illumination in the pupil (e.g., EC, polarization, double dark field, one-dimensional Fourier filtering, Fourier filtering, etc.). As shown in FIG. 7, light at field stop 80 has distribution 114, which is highly uniform across the field.

FIG. 8 illustrates simulated light distributions at various points in the embodiment of the system shown in FIG. 7, with the above-described optical design. These simulations were performed as described above. However, unlike the predetermined pattern of coherent light that was used for the simulations of FIG. 7, the predetermined pattern of coherent light used for the simulations of FIG. 8 is an annular pattern of light. In this manner, the simulation results shown in FIG. 8 may be used to estimate the light distribution in the system for EC mode inspection. In addition, the simulation results are shown in FIG. 8 for different system invariants. The system invariant may be changed to optimize light efficiency for different pixel sizes. The system invariants for which simulation results are shown in FIG. 8 are for pixel sizes of 225 nm, 150 nm, and 75 nm. The system invariant can be changed, for example, by reducing the size of the illumination patch on the diffuser while zooming the magnification to the field stop. The magnification may be zoomed by pupil lens 74 selected as a 3× zooming pupil lens for the simulations.

As shown in FIG. 8, a sharp image of the illumination patch on the diffuser is formed at the illumination pupil. In addition, as shown in FIG. 8, the total distribution of light at the illumination pupil is highly uniform. In this manner, the power density of light across the illumination pupil will be substantially uniform thereby minimizing the maximum power densities on all objective lens surfaces, the specimen, and sensor(s) of an inspection system. As such, the risk of coating damage to the objective lens due to pupil light distribution is minimized. Furthermore, the highly uniform light distribution at the illumination pupil shown in FIG. 8 illustrates that the illumination systems described herein can be used for efficient illumination of aperture modes of inspection such as EC, one-dimensional Fourier filtering, Fourier filtering, etc. and for efficient illumination at different system invariants.

Figure 9:
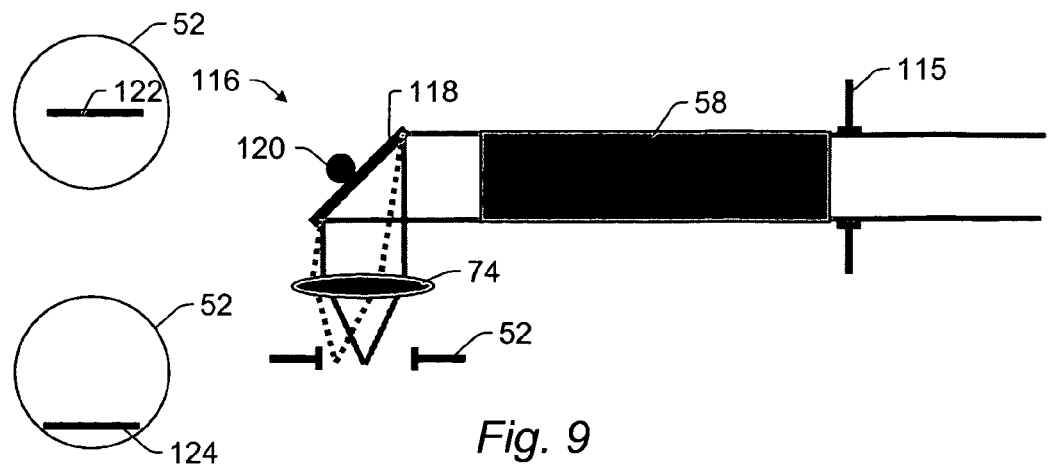
FIG. 9 is a schematic diagram illustrating a side view of one embodiment of a system that is configured to control one or more second optical elements to alter a lateral position of a predetermined pattern in an illumination pupil.

In some embodiments, the systems described herein may be configured to control one of the one or more second optical elements to alter a lateral position of the predetermined pattern in the illumination pupil. One such embodiment is illustrated in FIG. 9. In particular, as shown in FIG. 9, light enters homogenizer 58 at plane 115. Homogenizer 58 may be configured as described herein. Light exiting homogenizer 58 is directed to second optical element 116. Second optical element 116 may be a steering mirror. The steering mirror may be positioned at a field plane downstream of the homogenizer. The steering mirror may include reflective optical element 118 coupled to mechanism 120 that can be used to control a position of the reflective optical element. For example, one or more components of the system such as a processor (not shown in FIG. 9), which may be configured as described herein, may be coupled to mechanism 120 using any device and/or method known in the art. In this manner, the processor of the system may be configured to control mechanism 120 to thereby control a position of reflective optical element 118.

Light reflected by reflective optical element 118 is directed to illumination pupil 52 by collection lens 74, which may be configured as described herein. The position of reflective optical element 118 may, therefore, be controlled to alter a lateral position of the predetermined pattern in illumination pupil 52. For example, for line illumination of a specimen (not shown in FIG. 9), the position of reflective optical element 118 may be controlled such that the line illumination has lateral position 122 within illumination pupil 52. In this manner, the line illumination may be roughly centered in the illumination pupil. For other types of line illumination of a specimen, the position of reflective optical element 118 may be controlled such that the line illumination has lateral position 124 within illumination pupil 52. In this manner, the line illumination may be steered to the edge of the pupil. The line illumination may be steered to the edge of the pupil for certain inspection modes such as Fourier filtering modes of inspection and directional dark field modes of inspection. As such, the embodiment shown in FIG. 9 may be used to generate asymmetric pupil patterns by controlling a steering mirror or another suitable optical element positioned at a field plane downstream of the homogenizer. The embodiment shown in FIG. 9 may be included in any of the system embodiments described herein.

As described above, in some embodiments, the system may include a homogenizer disposed in an optical path of the one or more second optical elements. In one such embodiment, the system also includes one or more polarizing components positioned downstream of the homogenizer in the optical path. In this manner, polarization control of the illumination is performed downstream of the homogenizer to avoid the scrambling effects of the homogenizer. The one or more polarizing components may be configured to alter a polarization of the predetermined pattern of light. For example, the polarizing component(s) may be configured to maintain the linear polarization of the laser beam. The polarizing component(s) may also be configured to alter or control the orientation of the linear polarized laser beam (e.g., to provide linear horizontally oriented polarization or linear vertically oriented polarization). In addition, the polarizing component(s) may be configured to change the linear polarization of the laser beam to circular polarization. Therefore, such an embodiment of the illumination system may be used for polarization mode inspection.

Figure 10:
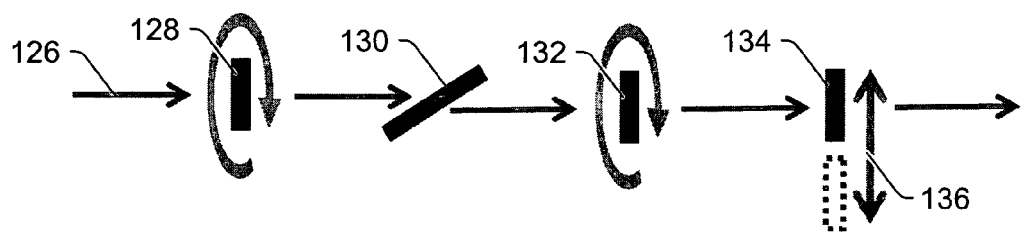
FIG. 10 is a schematic diagram illustrating a side view of one embodiment of one or more polarizing components that may be included in the system embodiments described herein.

One such embodiment of one or more polarizing components is illustrated in FIG. 10. As shown in FIG. 10, linearly polarized light 126 from a homogenizer (not shown in FIG. 10) is directed to polarizing component 128. Polarizing component 128 may be, for example, a rotatable half wave plate. Light exiting polarizing component 128 is directed to polarizing component 130. Polarizing component 130 may be, for example, a stationary plate polarizer. Polarizing component 128 may be used to control intensity by rotating the linear polarization relative to polarizing component 130. Polarizing component 130 may reduce any disruption in the polarization of the light caused by the diffuser (not shown in FIG. 10). Light exiting polarizing component 130 is directed to polarizing component 132. Polarizing component 132 may be a rotatable half wave plate that is configured to control the orientation of the linearly polarized light.

Light exiting polarizing component 132 may be directed to polarizing component 134. Polarizing component 134 may be a stationary quarter wave plate that may be used to alter the polarization of the light from linear to circular. Polarizing component 134 may, therefore, be inserted into the optical path of the system depending on the type of polarized illumination that is selected for inspection. For example, polarizing component 134 may be moved into and out of the optical path in the directions shown by arrow 136 using any device or method known in the art. The polarizing components shown in FIG. 10 may include any suitable polarizing components known in the art. Furthermore, although four polarizing components are shown in the embodiment of FIG. 10, it is to be understood that the system may include any appropriate number of polarizing components. The embodiment of FIG. 10 may be included in any of the system embodiments described herein.

As noted above, polarization control may be effectuated downstream of the homogenizing rod. However, it is noted that in embodiments of the system that include lens array(s) in place of a homogenizing rod or embodiments of the system that do not include a homogenizer, the polarization of the illumination will not be disrupted. As such, the polarization control may be effectuated at any position in the illumination system. In particular, the polarization components shown in FIG. 10 may be positioned at any appropriate point in the illumination system if the illumination system does not include a homogenizing rod.

Figure 11:
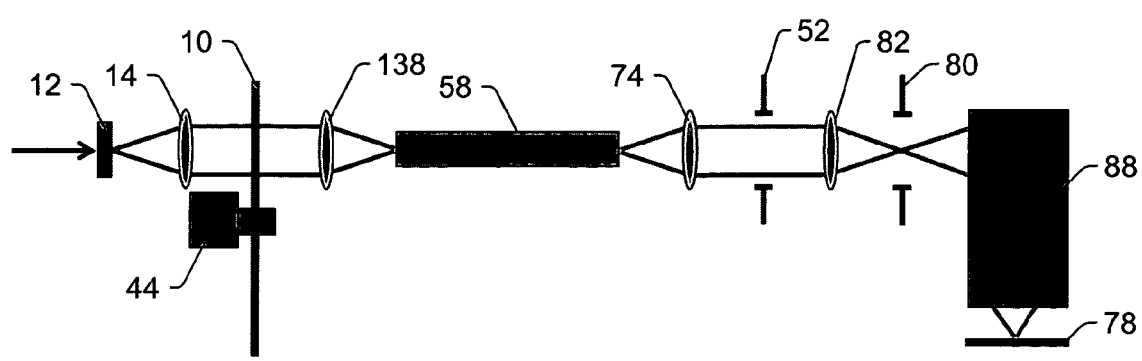
FIGS. 11-12 are schematic diagrams illustrating a side view of different embodiments of a system configured to provide illumination of a specimen for inspection.

FIG. 11 illustrates another embodiment of a system configured to provide illumination of a specimen for inspection. As shown in FIG. 11, this system includes diffractive optical element 12 configured to generate a predetermined pattern of coherent light. The system also includes optical component 14 configured to direct the predetermined pattern of coherent light to diffuser 10. Diffuser 10 may be coupled to motor 44 that is configured to rotate the diffuser. In addition, the system shown in FIG. 11 may be configured to alter a position of diffuser 10 in any other manner described herein during illumination of the specimen. Diffractive optical element 12, optical component 14, diffuser 10, and motor 44 may be further configured as described herein.

As shown in FIG. 11, light exiting diffuser 10 is directed to collection lens 138. Collection lens 138 is configured to position a Fourier transform plane of the diffuser at the entrance of homogenizer 58. Homogenizer 58 may be configured as described herein. Collection lens 138 may include any suitable collection lens known in the art. In addition, although collection lens 138 is shown in FIG. 11 to include only one lens, it is to be understood that the collection lens may include more than one optical element. Unlike the system shown in FIG. 1, the system shown in FIG. 11 does not include a second diffractive optical element positioned at an image plane of the diffuser.

Light exiting homogenizer 58 is collected by pupil lens 74 and directed into illumination pupil 52. Pupil lens 74 may be configured as described herein. Light exiting the illumination pupil is directed to field lens 82. Field lens 82 is configured to form an image of the homogenizer exit at field stop 80. Field lens 82 may be any appropriate refractive lens or reflective lens known in the art. The system includes objective lens 88 configured to focus light from the predetermined pattern from illumination pupil 52 onto specimen plane 78. Objective lens 88 may be configured as described above.

The etendue of the system shown in FIG. 11 may be altered in a number of different ways. For example, the etendue of the system may be altered by zooming or switching pupil lens 74 and switching diffractive optical element 12. Altering the etendue in this manner changes the number of homogenizer bounces and the size of the illuminated patch on the diffuser. In another example, the etendue of the system may be altered by changing the lateral size of homogenizer 58. Altering the etendue in this manner changes the number of homogenizer bounces, changes the degree of truncation of the spots at the homogenizer entrance, and may reduce the transmission at smaller pixel sizes. In an additional example, the etendue of the system may be altered by switching the homogenizer, switching the diffractive optical element, and zooming or switching collection lens 138. Altering the etendue of the system in this manner changes the number of homogenizer bounces and the size of the illuminated patch on the diffuser. The system shown in FIG. 11 may be further configured as described further herein. The system shown in FIG. 11 has all of the advantages of the systems described above.

Figure 12:
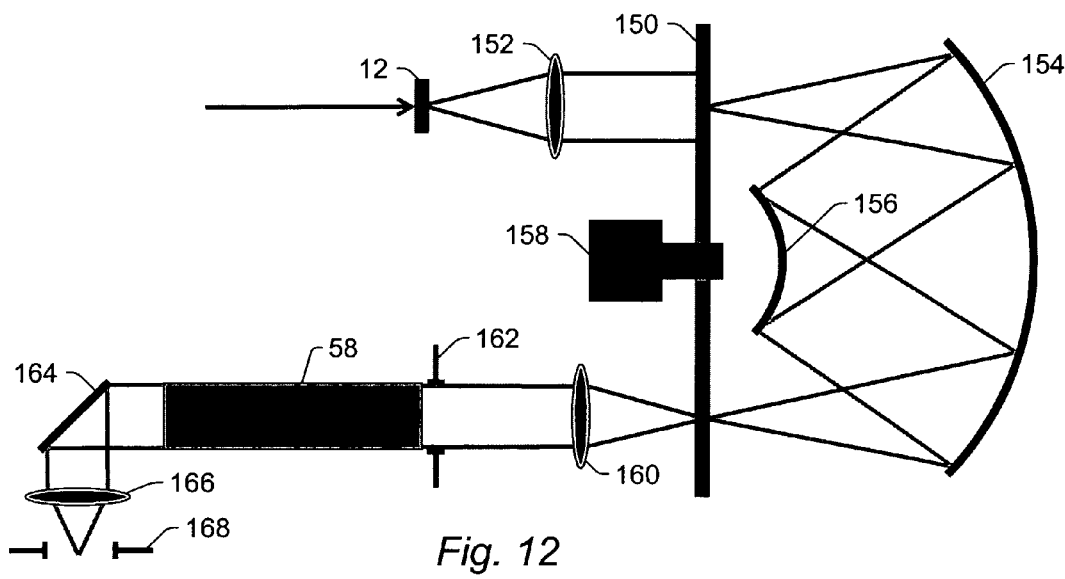

FIG. 12 illustrates another embodiment of a system configured to provide illumination of a specimen for inspection. This system includes one or more first optical elements configured to illuminate diffuser 150 with a predetermined pattern of coherent light. The one or more first optical elements of the system shown in FIG. 12 include diffractive optical element 12, which may be configured as described herein. The one or more first optical elements also include optical component 152 that is configured to produce a Fourier transform of diffractive optical element 12 on diffuser 150.

Diffuser 150 may be a ground glass diffuser or any other suitable diffuser known in the art. Light exiting diffuser 150 is directed back to diffuser 150 by reflective optical elements 154 and 156. Reflective optical elements 154 and 156 may form a 2-mirror 1× magnification relay that images the illumination back through the diffuser. Reflective optical elements 154 and 156 may include any suitable reflective optical elements known in the art.

In one embodiment, the system is configured to rotate diffuser 150 during illumination of the specimen. In one such example, diffuser 150 may be coupled to motor 158. Motor 158 may include any suitable device known in the art. In one example, motor 158 may be a self-feeding 23,000 rpm air spindle. Motor 158 may be further configured as described herein. In this manner, the system may be configured to rotate diffuser 150 during the integration time of a sensor (not shown in FIG. 12) used for inspection. As described above, the diffuser may be rotated such that the speckle pattern modulates and appears to "average out" over the integration time of the sensor. In addition, the system shown in FIG. 12 may be configured to include any other mechanism to alter a position of the diffuser as described further above during illumination of the specimen. The sensor may be further configured as described herein.

The system shown in FIG. 12 also includes one or more second optical elements configured to image light exiting the diffuser onto an illumination pupil of the system such that the predetermined pattern is reproduced in the illumination pupil and eventually in a pupil of an objective lens (not shown in FIG. 12). For example, as shown in FIG. 12, after passing through diffuser 150 twice, the light is directed to collection lens 160. Collection lens 160 is configured to produce a Fourier transform of diffuser 150 on plane 162 positioned at the entrance of homogenizer 58. Homogenizer 58 may be configured as described herein. Collection lens 160 may include any suitable lens or lenses known in the art.

Light exiting homogenizer 58 is imaged onto the specimen (not shown in FIG. 12). For example, the one or more second optical elements include reflective optical element 164 that is configured to direct the light exiting homogenizer 58 to pupil lens 166. Reflective optical element 164 may include any suitable reflective optical element known in the art. Pupil lens 166 is configured to focus the light from reflective optical element 164 into illumination pupil 168. The system shown in FIG. 12 may be further configured as described herein. The system shown in FIG. 12 has all of the advantages of the systems described above.

Another embodiment relates to a system configured to inspect a specimen. The system includes one or more first optical elements that are configured to illuminate a diffuser with a predetermined pattern of coherent light. The system also includes one or more second optical elements configured to image light exiting the diffuser onto an illumination pupil of the system such that the predetermined pattern is reproduced in the illumination pupil. In addition, the system includes an objective lens configured to focus light from the predetermined pattern in the illumination pupil onto a specimen plane. The system further includes a detection subsystem configured to generate output signals responsive to light propagating from the specimen plane. The output signals can be used to detect defects on the specimen.

Figure 13:
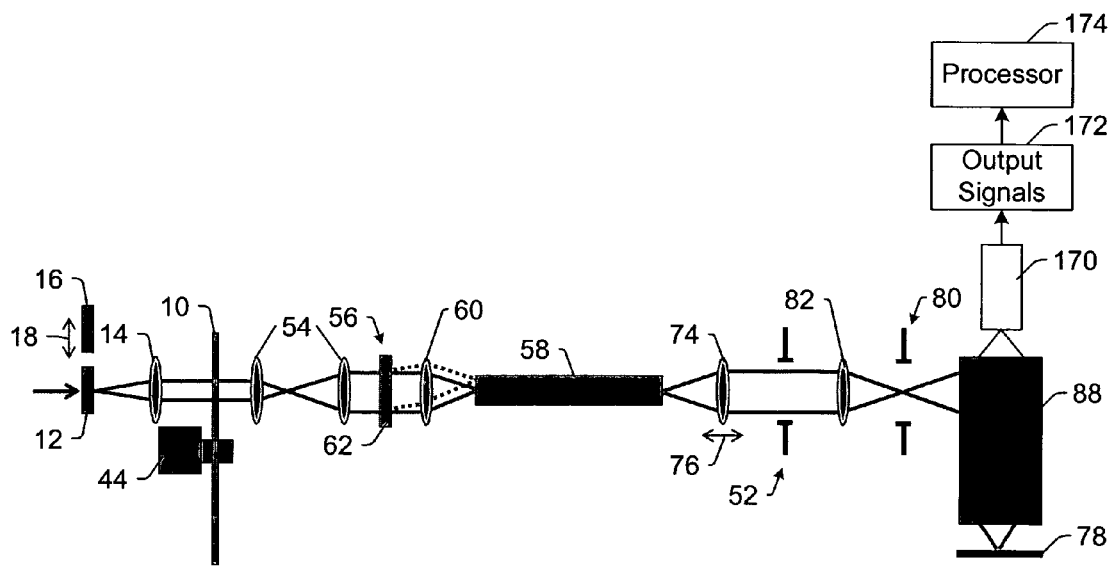
FIG. 13 is a schematic diagram illustrating a side view of one embodiment of a system configured to inspect a specimen.

One embodiment of such a system is illustrated in FIG. 13. In particular, the system shown in FIG. 13 includes one or more first optical elements, one or more second optical elements, and an objective lens that may be configured as described and shown in FIG. 1 and that are illustrated in FIGS. 1 and 13 using the same reference numerals. However, a system configured to inspect a specimen may include any other embodiments of a system configured to provide illumination of a specimen described herein.

As shown in FIG. 13, the system also includes detection subsystem 170. Detection subsystem 170 may include any appropriate detector known in the art such as a charge coupled device (CCD) or TDI camera. As shown in FIG. 13, the detection subsystem may be configured to detect light from specimen plane 78 that is collected by objective 88. In this manner, the detection subsystem may be configured to detect light reflected, diffracted, and/or scattered from the specimen plane at angles within the imaging NA of the objective. However, detection subsystem 170 may be configured to detect light reflected, diffracted, and/or scattered from the specimen plane at any selected angle. In addition, the system may include more than one detection subsystem (not shown), each of which is configured to detect light reflected, diffracted, and/or scattered from the specimen plane at different angles. The detection subsystems may otherwise be similarly configured. Alternatively, the detection subsystems may be differently configured.

Detection subsystem 170 is also configured to generate output signals 172 that are responsive to light propagating from the specimen plane. Output signals 172 generated by detection subsystem 170 can be used to detect defects on the specimen. For example, the system may include processor 174. Processor 174 may be coupled to detection subsystem 170 by a transmission medium (not shown). The transmission medium may include any suitable transmission medium known in the art. In addition, the processor may be coupled to the detection subsystem by one or more electronic components (not shown) such as an analog-to-digital converter. In this manner, processor 174 is configured to receive output signals 172 from detection subsystem 170.

Processor 174 may be configured to use the output signals to detect defects on the specimen. In addition, the processor may be configured to use the output signals and any method and/or algorithm known in the art to detect the defects on the specimen. Furthermore, processor 174 may be configured to perform any other inspection-related functions known in the art (e.g., defect location determination, defect classification, defect mapping, etc.).

Processor 174 may take various forms, including a personal computer system, mainframe computer system, workstation, image computer, parallel processor, or any other device known in the art. In general, the term "computer system" may be broadly defined to encompass any device having one or more processors, which executes instructions from a memory medium. The system shown in FIG. 13 may be further configured as described herein. The system shown in FIG. 13 has all of the advantages of the systems described above.

In some embodiments, the inspection systems described herein may be configured as "stand alone tools" or tools that are not physically coupled to a process tool. However, such a system may be coupled to a process tool (not shown) by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a cluster tool or a number of process modules coupled by a common handler. Alternatively, the inspection systems described herein may be integrated into a process tool such as those described above.

The results of inspection performed by the systems described herein may be used to alter a parameter of a process or a process tool using a feedback control technique, a feedforward control technique, and/or an in situ control technique. The parameter of the process or the process tool may be altered manually or automatically.

Another embodiment relates to a method for providing illumination of a specimen for inspection. The method includes illuminating a diffuser with a predetermined pattern of coherent light. The method also includes imaging light exiting the diffuser onto an illumination pupil such that the predetermined pattern is reproduced in the illumination pupil. In addition, the method includes focusing light from the predetermined pattern in the illumination pupil onto a specimen plane. For example, the method may include mapping light from the predetermined pattern in the illumination pupil into specific angles at a specimen plane. This method may be performed by any of the system embodiments described herein.

This method may also include any additional steps described herein. For instance, in one embodiment, the method includes altering a position of the diffuser (e.g., rotating, modulating, translating, or vibrating the diffuser) during the illumination of the specimen. In another embodiment, the method includes selecting the predetermined pattern from different patterns of light that can be used to illuminate the diffuser. In an additional embodiment, the method includes positioning one of multiple diffractive optical elements in an optical path of the light illuminating the diffuser based on the predetermined pattern and different patterns of light that can be generated by the multiple diffractive optical elements.

In some embodiments, the method includes imaging a Fourier plane of the diffuser onto an entrance of a homogenizer. In one such embodiment, a distribution of the light exiting the diffuser is truncated at an entrance of the homogenizer. In another such embodiment, the method includes controlling an optical element to alter a magnification of the light exiting the homogenizer. In a further embodiment, the method includes controlling one or more optical elements to alter a size of an area on the diffuser that is illuminated with the predetermined pattern of light.

In an additional embodiment, the method includes altering a distribution of the light exiting the diffuser at an entrance of a homogenizer such that the light at the entrance of the homogenizer has a substantially uniform distribution. In some embodiments, the method includes directing the light exiting the diffuser to two or more homogenizers simultaneously and directing light exiting the two or more homogenizers to the illumination pupil simultaneously.

In an additional embodiment, illuminating the diffuser includes illuminating the diffuser with the predetermined pattern of coherent light at a first position and illuminating the diffuser at a second position with light exiting the first position of the diffuser. The first and second positions are spatially separated across the diffuser. In a different embodiment, illuminating the diffuser includes illuminating an additional diffuser with the predetermined pattern of coherent light and illuminating the diffuser with light exiting the additional diffuser in the predetermined pattern.

In one embodiment, the method includes altering a polarization of the predetermined pattern of light downstream of a homogenizer. In another embodiment, the method includes controlling an optical element to alter a lateral position of the predetermined pattern of the illumination pupil. In an additional embodiment, due to movement of the diffuser, the light on the specimen plane is not substantially coherent. In some embodiments, the method includes selecting a predetermined pattern based on an illumination mode selected for the inspection of the specimen. In a further embodiment, the predetermined pattern of coherent light has a wavelength below about 270 nm. Each of the embodiments of the method described above may include any other step(s) described herein. The methods described above have all of the advantages of the systems described above.

Further modifications and alternative embodiments of various aspects of the invention may be apparent to those skilled in the art in view of this description. For example, systems and methods for providing illumination of a specimen for inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to provide illumination of a specimen for inspection, comprising:

one or more first optical elements configured to illuminate a diffuser with a predetermined pattern of coherent light;

one or more second optical elements configured to image light exiting the diffuser onto an illumination pupil of the system such that the predetermined pattern is reproduced in the illumination pupil; and an objective lens configured to focus light from the predetermined pattern in the illumination pupil onto a specimen plane.

2. The system of claim 1, wherein the system is further configured to alter a position of the diffuser during the illumination of the specimen.

3. The system of claim 1, wherein the one or more first optical elements comprise a diffractive optical element configured to generate the predetermined pattern of coherent light.

4. The system of claim 1, wherein the one or more first optical elements comprise a diffractive optical element configured to generate the predetermined pattern of coherent light and to generate different patterns of coherent light that can be selected to illuminate the diffuser.

5. The system of claim 1, wherein the one or more first optical elements comprise diffractive optical elements, wherein each of the diffractive optical elements is configured to illuminate the diffuser with a different pattern, and wherein the system is further configured to position one of the diffractive optical elements in an optical path of the system based on the predetermined pattern and the different patterns of the diffractive optical elements.

6. The system of claim 1, further comprising a homogenizer disposed in an optical path of the one or more second optical elements, wherein the one or more second optical elements are further configured to image a Fourier plane of the diffuser onto an entrance of the homogenizer.

7. The system of claim 1, further comprising a homogenizer disposed in an optical path of the one or more second optical elements such that a distribution of the light exiting the diffuser is truncated at an entrance of the homogenizer.

8. The system of claim 1, further comprising a homogenizer disposed in an optical path of the one or more second optical elements, wherein the system is further configured to control at least one of the one or more second optical elements to alter a magnification of light exiting the homogenizer.

9. The system of claim 1, wherein the system is further configured to control one of the one or more first optical elements to alter a size of an area on the diffuser illuminated by the one or more first optical elements.

10. The system of claim 1, further comprising a diffractive optical element and a homogenizer disposed in an optical path of the one or more second optical elements, wherein the diffractive optical element is positioned at an image plane of the diffuser and is configured to distribute the light exiting the diffuser substantially uniformly at an entrance of the homogenizer.

11. The system of claim 1, further comprising two or more homogenizers, wherein the one or more second optical elements are further configured to direct the light exiting the diffuser to the two or more homogenizers simultaneously and to direct light exiting the two or more homogenizers to the illumination pupil simultaneously.

12. The system of claim 1, further comprising a homogenizer disposed in an optical path of the one or more second optical elements, wherein the homogenizer comprises a homogenizing rod.

13. The system of claim 1, further comprising a homogenizer disposed in an optical path of the one or more second optical elements, wherein the homogenizer comprises a homogenizing tunnel.

14. The system of claim 1, further comprising a homogenizer disposed in an optical path of the one or more second optical elements, wherein the homogenizer comprises one or more arrays of lenses.

15. The system of claim 1, wherein the one or more first optical elements are further configured to illuminate the diffuser with the predetermined pattern of coherent light at a first position and to illuminate the diffuser at a second position with light exiting the first position of the diffuser, and wherein the first and second positions are spatially separated across the diffuser.

16. The system of claim 1, further comprising an additional diffuser, wherein the one or more first optical elements are further configured to illuminate the additional diffuser with the predetermined pattern of coherent light and to illuminate the diffuser with light exiting the additional diffuser in the predetermined pattern.

17. The system of claim 1, further comprising a homogenizer disposed in an optical path of the one or more second optical elements and one or more polarizing components positioned downstream of the homogenizer in the optical path, wherein the one or more polarizing components are configured to alter a polarization of the predetermined pattern of light.

18. The system of claim 1, wherein the system is further configured to control one of the one or more second optical elements to alter a lateral position of the predetermined pattern in the illumination pupil.

19. The system of claim 1, wherein the light focused onto the specimen plane is not substantially coherent.

20. The system of claim 1, wherein the predetermined pattern is selected based on an illumination mode selected for the inspection of the specimen.

21. The system of claim 1, wherein the system further comprises a laser light source configured to direct coherent light having a wavelength below about 270 nm to the one or more first optical elements.

22. The system of claim 1, wherein the coherent light comprises multiple wavelengths of coherent light, and wherein the light focused from the predetermined pattern in the illumination pupil onto the specimen plane comprises the multiple wavelengths of coherent light.

23. The system of claim 1, wherein the coherent light comprises multiple wavelengths of coherent light, and wherein the light focused from the predetermined pattern in the illumination pupil onto the specimen plane comprises fewer than all of the multiple wavelengths of coherent light.

24. The system of claim 1, further comprising a lamp light source, wherein the system is further configured to simultaneously focus light from the lamp light source and the light from the predetermined pattern in the illumination pupil onto the specimen plane.

25. A system configured to inspect a specimen, comprising:
one or more first optical elements configured to illuminate a diffuser with a predetermined pattern of coherent light;
one or more second optical elements configured to image light exiting the diffuser onto an illumination pupil of the system such that the predetermined pattern is reproduced in the illumination pupil;
an objective lens configured to focus light from the predetermined pattern in the illumination pupil onto a specimen plane; and
a detection subsystem configured to generate output signals responsive to light propagating from the specimen plane, wherein the output signals can be used to detect defects on the specimen.

26. A method for providing illumination of a specimen for inspection, comprising:
illuminating a diffuser with a predetermined pattern of coherent light;
imaging light exiting the diffuser onto an illumination pupil such that the predetermined pattern is reproduced in the illumination pupil; and
focusing light from the predetermined pattern in the illumination pupil onto a specimen plane.

27. A system configured to provide illumination of a specimen for inspection, comprising:
one or more first optical elements configured to illuminate a diffuser with a predetermined pattern of low spatial coherence light;
one or more second optical elements configured to image light exiting the diffuser onto an illumination pupil of the system such that the predetermined pattern is reproduced in the illumination pupil; and
an objective lens configured to focus light from the predetermined pattern in the illumination pupil onto a specimen plane.

28. The system of claim 27, wherein a position of the diffuser during the illumination is substantially stationary.

* * * * *